(12) United States Patent
Matsuzawa et al.

(10) Patent No.: US 7,722,808 B2
(45) Date of Patent: May 25, 2010

(54) METHOD AND KITS FOR STERILIZING AND STORING SOFT CONTACT LENSES

(75) Inventors: Yasuo Matsuzawa, Roswell, GA (US); Nicolae Enciu, Duluth, GA (US); Celeste Aguado, Atlanta, GA (US)

(73) Assignee: Novartis AG, Basel (CH)

( * ) Notice: Subject to any disclaimer, the term of this patent is extended or adjusted under 35 U.S.C. 154(b) by 539 days.

(21) Appl. No.: 10/936,032

(22) Filed: Sep. 8, 2004

(65) Prior Publication Data

US 2005/0056553 A1 Mar. 17, 2005

Related U.S. Application Data

(60) Provisional application No. 60/502,745, filed on Sep. 12, 2003.

(51) Int. Cl.
*A61L 2/00* (2006.01)
(52) U.S. Cl. .............. 422/28; 422/22; 250/455.11; 206/5.1
(58) Field of Classification Search .............. 206/5.1; 422/28, 22; 250/455.11
See application file for complete search history.

(56) References Cited

U.S. PATENT DOCUMENTS

| | | | |
|---|---|---|---|
| 4,002,234 A | 1/1977 | Loshack | 206/205 |
| 4,122,942 A | 10/1978 | Wolfson | 206/5.1 |
| 4,529,535 A * | 7/1985 | Sherman | 514/272 |
| 4,691,820 A | 9/1987 | Martinez | 206/205 |
| 5,054,610 A | 10/1991 | Ajello | 206/5.1 |
| 5,141,665 A | 8/1992 | Sherman | 252/106 |
| 5,171,267 A | 12/1992 | Ratner et al. | 623/6 |
| 5,310,429 A | 5/1994 | Chou et al. | 134/6 |
| 5,368,815 A | 11/1994 | Kasting, Jr. et al. | 422/3 |
| 5,375,698 A | 12/1994 | Ewart et al. | 206/5.1 |
| 5,409,104 A | 4/1995 | Lovell | 206/5.1 |
| 5,467,868 A | 11/1995 | Abrams et al. | 206/5.1 |
| 5,598,316 A | 1/1997 | Kasting, Jr. | 361/212 |
| 5,598,919 A | 2/1997 | Taylor | 206/5.1 |
| 5,604,189 A | 2/1997 | Zhang et al. | 510/112 |
| 5,609,246 A | 3/1997 | Borghorst et al. | 206/5.1 |
| 5,618,492 A | 4/1997 | Auten et al. | 422/22 |
| 5,697,495 A | 12/1997 | Abrams et al. | 206/5.1 |
| 5,700,559 A * | 12/1997 | Sheu et al. | 428/319.7 |
| 5,704,468 A | 1/1998 | Lust et al. | 206/5.1 |
| 5,722,536 A | 3/1998 | Pierce et al. | 206/5.1 |
| 5,726,733 A * | 3/1998 | Lai et al. | 351/160 R |
| 5,773,396 A | 6/1998 | Zhang et al. | 510/115 |
| 5,800,807 A | 9/1998 | Hu et al. | 424/78.04 |
| 5,804,107 A | 9/1998 | Martin et al. | 264/1.36 |
| 5,823,327 A | 10/1998 | Wu et al. | 206/5.1 |
| 5,882,687 A | 3/1999 | Park et al. | 424/682 |
| 5,942,558 A | 8/1999 | Korb | 523/106 |
| 5,983,608 A | 11/1999 | Wu et al. | 53/478 |
| 6,029,808 A | 2/2000 | Peck et al. | 206/210 |
| 6,039,899 A | 3/2000 | Martin et al. | 264/1.36 |
| 6,044,966 A | 4/2000 | Haase | 206/5.1 |
| 6,082,533 A | 7/2000 | Smith et al. | 206/210 |
| 6,105,342 A | 8/2000 | Hansen et al. | 53/452 |
| 6,121,327 A | 9/2000 | Tsuzuki et al. | 514/642 |
| 6,200,626 B1 | 3/2001 | Grobe, III et al. | 427/2.24 |
| 6,248,266 B1 * | 6/2001 | Gartley et al. | 264/1.36 |
| 6,253,912 B1 | 7/2001 | O'Neill et al. | 206/5.1 |
| 6,260,695 B1 | 7/2001 | Tasbar et al. | 206/5.1 |
| 6,274,133 B1 | 8/2001 | Hu et al. | 424/78.04 |
| 6,348,507 B1 | 2/2002 | Heiler et al. | 514/769 |
| 6,398,018 B1 | 6/2002 | Livesly et al. | 206/210 |
| 6,440,366 B1 | 8/2002 | Salpekar et al. | 422/40 |
| 6,471,052 B2 | 10/2002 | Faxe et al. | 206/5.1 |
| 6,474,465 B1 | 11/2002 | Jux | 206/5.1 |
| 6,511,617 B1 | 1/2003 | Martin et al. | 264/1.36 |
| 6,531,432 B2 | 3/2003 | Molock et al. | 510/112 |
| 6,599,559 B1 | 7/2003 | Mcgee et al. | 427/2.24 |
| 6,638,563 B2 | 10/2003 | Mcgee et al. | 427/2.24 |
| 6,699,435 B2 | 3/2004 | Salpekar et al. | 422/40 |
| 6,702,983 B2 | 3/2004 | Hu et al. | 422/1 |
| 6,805,836 B2 | 10/2004 | Salamone et al. | 422/1 |
| 7,037,469 B2 | 5/2006 | Hu et al. | 422/28 |
| 2002/0182315 A1 | 12/2002 | Heiler et al. | 427/162 |
| 2002/0197478 A1 | 12/2002 | Muggli et al. | 428/411.1 |
| 2003/0029736 A1 | 2/2003 | Phillips et al. | 206/5.1 |
| 2003/0030161 A1 | 2/2003 | Pegram et al. | 264/2.5 |
| 2003/0038388 A1 | 2/2003 | Pegram et al. | 264/2.5 |

(Continued)

FOREIGN PATENT DOCUMENTS

EP 0 223 581 5/1993

(Continued)

OTHER PUBLICATIONS

International Search Report.

(Continued)

*Primary Examiner*—Sean E Conley
(74) *Attorney, Agent, or Firm*—Jian Zhou; Robert A. Ambrose

(57) ABSTRACT

The present invention provides a method and a container for sterilizing a soft contact lens and for providing a sterilized storage package of the soft contact lens maintained in a packaging solution. By using the method and container of the invention, deformations of soft contact lenses during autoclave can be substantially reduced.

22 Claims, No Drawings

U.S. PATENT DOCUMENTS

| | | | |
|---|---|---|---|
| 2003/0057111 A1 | 3/2003 | Ichikawa et al. | 206/5.1 |
| 2003/0068433 A1 | 4/2003 | Mcgee et al. | 427/162 |
| 2003/0129083 A1 | 7/2003 | Graham et al. | 422/42 |
| 2003/0130144 A1 | 7/2003 | Alvarez et al. | 510/112 |
| 2003/0145940 A1 | 8/2003 | Chaudhury et al. | 156/272.6 |
| 2003/0235604 A1 | 12/2003 | Mcgee et al. | 424/429 |
| 2004/0091613 A1 | 5/2004 | Wood et al. | 427/162 |
| 2004/0120916 A1 | 6/2004 | Huth | 424/70.13 |
| 2004/0137079 A1 | 7/2004 | Cook et al. | 424/662 |
| 2005/0119141 A1 | 6/2005 | Quenville et al. | 510/112 |
| 2005/0260280 A1 | 11/2005 | Cook et al. | 424/661 |
| 2005/0266089 A1 | 12/2005 | Cook et al. | 424/488 |
| 2006/0094643 A1 | 5/2006 | Svirkin et al. | 514/8 |
| 2006/0135381 A1 | 6/2006 | Hu et al. | 510/112 |

FOREIGN PATENT DOCUMENTS

| | | |
|---|---|---|
| EP | 0 884 962 | 1/1997 |
| EP | 0 604 177 | 6/1999 |
| EP | 0 745 536 | 1/2000 |
| EP | 1 277 416 | 1/2003 |
| WO | WO 93/15972 | 8/1993 |
| WO | WO 94/24019 | 10/1994 |
| WO | WO 97/18997 | 5/1997 |
| WO | WO 97/20019 | 6/1997 |
| WO | WO 98/21995 | 5/1998 |
| WO | WO 99/27813 | 6/1999 |
| WO | WO 03/016175 | 2/2003 |
| WO | WO 03/039969 | 5/2003 |
| WO | WO 2006/088758 | 8/2006 |

OTHER PUBLICATIONS

Written Opinion of the International Searching Authority.
European Search Report.
Search Report I.

* cited by examiner

METHOD AND KITS FOR STERILIZING AND STORING SOFT CONTACT LENSES

This application claims the benefit under 35 USC §119 (e) of U.S. provisional application No. 60/502,745, filed Sep. 12, 2003, incorporated by reference in its entirety.

The present invention is related to a method for sterilizing soft contact lenses, in particular silicone or silicone hydrogel contact lenses. In addition, the present invention is related to containers for sterilizing and storing soft contact lenses.

BACKGROUND OF THE INVENTION

Hydrophilic contact lenses, which may be disposable after a single wear or short-term use, have become quite popular because of comfort and convenience. Generally, such hydrophilic contact lenses are manufactured from suitable hydrophilic polymeric materials. These materials may be, amongst others, copolymers of hydroxyethyl methacrylate containing from about 20% to 90% or more of water, depending upon the polymer composition. Generally, such hydrophilic contact lenses must be stored in a sterile aqueous solution, usually in isotonic saline solution in order to prevent dehydration and to maintain the lenses in a ready-to-wear condition. In order to maintain this high water content, hydrophilic lenses are typically immersed in a sterile, aqueous solution within a water-tight package during storing, shipping, and handling processes.

The packaging of hydrophilic contact lenses in a sterile aqueous solution is well known in the contact lens manufacturing technology. There have been a variety of packages used to store hydrophilic contact lenses. In particular, so-called blister packages are widely used for the storage and dispensing of the hydrophilic contact lenses. Typically, the blister package for storing and dispensing a hydrophilic contact lens includes an injection-molded or thermoformed plastic base portion incorporating a molded cavity which is surrounded by an outstanding planar flange about the rim of the cavity. The plastic base portion is made of hydrophobic material. A flexible cover sheet is adhered to the surface of the flange so as to sealingly enclose the cavity in a generally liquid-tight mode. Within the cavity of the base portion, a hydrophilic contact lens is immersed in a sterile aqueous solution, such as an isotonic saline solution.

More recently, with the recent developments in new silicone hydrogels, soft contact lenses made of such silicon hydrogels and having hydrophilic coatings are increasing in popularity, since such lenses have high oxygen permeability, high water content, high ion permeability, all of which are required to maintain corneal health and wear comfort. Like hydrophilic contact lens, such silicone hydrogel lenses typically are already hydrated and packaged in a sterile aqueous solution and therefore can be immediately worn upon purchase, by merely removing the lens from the package, without any subsequent treatment of the lens or additional preparation by the consumer. In general, packages traditionally for hydrophilic contact lenses are used to store and dispense silicon hydrogel contact lenses. However, there are problems associated with use of traditional lens packages for storing and dispensing silicon hydrogel lenses.

Contact lenses, which are hydrated and packaged in solution, must be sterilized. Sterilization of the hydrated lenses during manufacturing and packaging is typically accomplished by autoclaving. The autoclaving process involves heating the packaging of a contact lens to a temperature of about 121° C. for approximately 20 minutes under pressure. It has been found that autoclaving of a silicone hydrogel lens packaged in a plastic package can cause deformations of a silicone hydrogel lens. Such deformations can affect the production yield of contact lenses and increase production cost.

Therefore, there is a need for a method of sterilizing silicon hydrogel contact lenses. There is also a need for improved packages for storing and dispensing silicon hydrogel contact lenses.

SUMMARY OF THE INVENTION

The present invention, in one aspect, provides a method of sterilizing a soft contact lens and providing a sterilized storage package of the soft contact lens maintained in a packaging solution, comprising the steps of: (a) providing a container having a cavity for receiving a packaging solution and a soft contact lens having a core polymeric material and a hydrophilic coating thereon, wherein the surface of the cavity is modified by surface treatment to hydrophilic so that deformations of the soft contact lenses, caused during autoclaving by air bubbles formed between the cavity surface and the hydrophilic coating due to mismatch in surface hydrophilicity and/or by adherence of the soft contact lens to the cavity surface, are substantially reduced; (b) placing an amount of the packaging solution and the soft contact lens in the container, wherein the amount of the packaging solution is sufficient to have the soft contact lens to be fully immersed; (c) sealing said container to form a storage package of the soft contact lens; and (d) autoclaving said package to obtain the sterilized storage package of the soft contact lens.

The present invention, in another aspect, provides a container for autoclaving and storing a soft contact lens in a packaging solution, wherein the soft contact lens has a core polymeric material and a hydrophilic coating thereon. The container of the invention comprises a base and a cover, wherein the cover is detachably sealed to the base, wherein the base includes a cavity for receiving a sterile packaging solution and the contact lens, wherein the surface of the cavity is modified by surface treatment to hydrophilic so that deformations of the contact lenses caused during autoclaving by air bubbles formed between the cavity surface and the hydrophilic coating due to mismatch in surface hydrophilicity and/or by adherence of the soft contact lens to the cavity surface can be substantially reduced.

DETAILED DESCRIPTION OF THE INVENTION

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

"Contact lenses" refers to ophthalmic devices that resides on the eye or ocular vicinity for vision correction, diagnosis, sample collection, drug delivery, wound healing, cosmetic appearance (e.g., eye color modification), or other ophthalmic applications. In accordance with the present invention, a soft contact lens comprises a core polymeric material and a hydrophilic coating thereon. The core polymeric material can be a silicone elastomer, a silicone hydrogel, a fluorohydrogel, or a fluorosilicone hydrogel.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers. A silicone hydrogel, a fluorohydrogel, or a fluorosilicone hydrogel can be prepared according to any methods known to a person skilled in the art.

A "monomer" means a low molecular weight compound that can be polymerized. Low molecular weight typically means average molecular weights less than 700 Daltons.

A "hydrophilic monomer" refers to a monomer which as a homopolymer typically yields a polymer that is water-soluble or can absorb at least 10 percent by weight water.

A "macromer" refers to medium and high molecular weight compounds or polymers that contain functional groups capable of further polymerization. Medium and high molecular weight typically means average molecular weights greater than 700 Daltons. "Polymer" means a material formed by polymerizing one or more monomers.

A "hydrophilic coating" in reference to a soft contact lens means an ophthalmically compatible surface which is obtained by surface treatment and is more hydrophilic than the core polymeric material of the soft contact lens.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) and/or conjunctiva which may come into intimate contact with a contact lens.

"Surface treatment", as used herein, means a surface modification process in which an article, e.g., a contact lens, has been treated by means of contact with a vapor or liquid, and/or by means of application of an energy source to (1) apply a coating to the surface of an article, (2) deposit (by absorption) chemical species onto the surface of an article, (3) alter the chemical nature (e.g., electrostatic charge) of chemical groups on the surface of an article, or (4) modify the surface properties of an article. Exemplary surface treatment include, but are not limited to, a surface treatment by energy (e.g., a plasma, a corona discharge, a flame treatment, a static electrical charge, irradiation, or other energy source), chemical treatments (e.g., acid surface etching), the grafting of hydrophilic monomers or macromers onto the surface of an article, and layer-by-layer deposition of charged and/or non-charged polymeric materials. A preferred class of surface treatments are plasma treatments, in which an ionized gas is applied to the surface of an article to form a plasma polymer coating. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to an article, e.g., a contact lens, and is obtained through a layer-by-layer ("LbL") deposition of one or more polyionic or charged materials on an article. An LbL coating can be composed of one or more layers, preferably one or more bilayers. Formation of an LbL coating on an ophthalmic device may be accomplished in a number of ways, for example, as described in U.S. Pat. No. 6,451,871 (herein incorporated by reference in its entirety) and U.S. Pat. Nos. 6,719,929; 6,793,973; and 6,926,965, herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

The term "bilayer" is employed herein in a broad sense and is intended to encompass: a coating structure formed on a contact lens by alternatively applying, in no particular order, one layer of a first polyionic material (or charged material) and subsequently one layer of a second polyionic material (or charged material) having charges opposite of the charges of the first polyionic material (or the charged material); or a coating structure formed on a contact lens by alternatively applying, in no particular order, one layer of a first charged polymeric material and one layer of a non-charged polymeric material or a second charged polymeric material. It should be understood that the layers of the first and second coating materials (described above) may be intertwined with each other in the bilayer.

A contact lens having a core material and an LbL coating, which comprises at least one layer of a charged polymeric material and one layer of a non-charged polymeric material that can be non-covalently bonded to the charged polymeric material, can be prepared according to a method disclosed in a co-pending U.S. application, U.S. Pat. No. 6,926,965, entitled "LbL-COATED MEDICAL DEVICE AND METHOD FOR MAKING THE SAME", herein incorporated by reference in its entirety.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

The "cavity surface" or "the surface of the cavity" in reference to a container for sterilizing and/or storing a soft contact lens means the surface which can be in direct contact with a sterile packaging solution held therein.

An "average contact angle" refers to a contact angle of water on a surface of a material (measured by Sessile Drop method), which is obtained by averaging measurements of at least 3 individual contact lenses. Average contact angles (Sessile Drop) of contact lenses can be measured using a VCA 2500 XE contact angle measurement device from AST, Inc., located in Boston, Mass. This equipment is capable of measuring advancing or receding contact angles or sessile (static) contact angles. The measurements are preferably performed on fully hydrated materials.

Contact angle is a general measure of the surface hydrophilicity of a contact lens or an article (e.g., the cavity surface of a container). In particular, a low contact angle corresponds to more hydrophilic surface.

"Hydrophilic" in reference to a surface or material means an averaged contact angle of less than about 80 degrees, preferably less than about 70 degrees, more preferably less than about 60 degrees.

The present invention generally is related to a method and kits for sterilizing soft contact lenses. By using the method of the invention, deformations of soft contact lenses during autoclave can be substantially reduced. The present invention is largely based on recognition that deformations of soft contact lenses during autoclave are resulted from mismatch in hydrophilicity between the hydrophilic coating of a soft contact lens and the contacting cavity surface of a container for storing the soft contact lens and/or from adherence of the soft contact lens to the cavity surface.

It is believed that, since a conventional container has a hydrophobic cavity surface whereas a soft contact lens has a hydrophilic coating, air can be trapped between the cavity surface and the hydrophilic coating in an area where the soft contact lens contacts the cavity surface. The trapped air can become a spot where distortions in some local surface areas of a soft contact lens can occurs. During autoclaving (heat cycles), those distortions may cause deformations of the soft contact lens because of its memory characteristics.

It is also possible that a soft contact lens may undergo shrinking and swelling under autoclaving conditions. The soft contact lens may adhere to the cavity surface of a container during shrinking and swelling processes and therefore may also cause deformation of a soft contact lens during autoclave.

To significantly reduce the deformations of soft contact lenses during autoclaving, Applicants have developed a method and containers for sterilizing and storing soft contact lenses.

A method of the invention for sterilizing a soft contact lens and providing a sterilized storage package of the soft contact lens maintained in a packaging solution, comprises the steps of: (a) providing a container having a cavity for receiving a packaging solution and a soft contact lens having a core polymeric material and a hydrophilic coating thereon, wherein the cavity has an cavity surface which is modified by surface treatment to hydrophilic so that deformations of the soft contact lenses, caused during autoclaving by air bubbles formed between the cavity surface and the hydrophilic coating due to mismatch in surface hydrophilicity and/or by adherence of the soft contact lens to the cavity surface, are substantially reduced; (b) placing an amount of the packaging solution and the soft contact lens in the container, wherein the amount of the packaging solution is sufficient to have the soft contact lens to be fully immersed; (c) sealing said container to form a storage package of the soft contact lens; and (d) autoclaving said package to obtain the sterilized storage package of the soft contact lens.

A container of the invention for autoclaving and storing a soft contact lens having a core polymeric material and a hydrophilic coating in a packaging solution, comprises a base and a cover, wherein the cover is detachably sealed to the base, wherein the base includes a cavity for receiving a sterile packaging solution and the contact lens, wherein the cavity has an cavity surface which is modified by surface treatment to hydrophilic so that deformations of the contact lenses caused during autoclaving by air bubbles formed between the cavity surface and the hydrophilic coating due to mismatch in surface hydrophilicity and/or by adherence of the soft contact lens to the cavity surface can be substantially reduced.

The core polymeric material of a soft contact lens is preferably a silicon hydrogel. Preferably, the silicone hydrogel is prepared by curing in a mold a polymerizable composition comprising a siloxane-containing macromer and/or a siloxane-containing monomer and hydrophilic monomers. Any know suitable siloxane-containing macromer can be used to prepare soft contact lenses. A particularly preferred siloxane-containing macromer is selected from the group consisting of Macromer A, Macromer B, Macromer C, and Macromer D described in U.S. Pat. No. 5,760,100, herein incorporated by reference in its entirety. Any known suitable siloxane-containing monomers can be used to prepare soft contact lenses. Examples of siloxane-containing monomers include, without limitation, methacryloxyalkylsiloxanes, tristrimethylsilyloxysilylpropyl methacrylate (TRIS), 3-methacryloxy propylpentamethyldisiloxane and bis(methacryloxypropyl)tetramethyl-disiloxane. A preferred siloxane-containing monomer is TRIS, which is referred to 3-methacryloxypropyltris(trimethylsiloxy)silane, and represented by CAS No. 17096-07-0. The term "TRIS" also includes dimers of 3-methacryloxypropyltris(trimethylsiloxy)silane.

More preferably, the core polymeric material is prepared by curing in a mold any formulations for making soft contact lenses. Exemplary formulations include without limitation the formulation of lotrafilcon A, lotrafilcon B, etafilcon A, genfilcon A, lenefilcon A, acquafilcon A, and balafilcon.

In accordance with the present invention, a packaging solution is ophthalmically compatible, meaning that a contact lens treated with the solution is generally suitable and safe for direct placement on the eye without rinsing, that is, the solution is safe and comfortable for contact with the eye via a contact lens that has been wetted with the solution. A packaging solutions of the invention may be any water-based solution that is used for the storage of contact lenses. Typical solutions include, without limitation, saline solutions, other buffered solutions, and deionized water. The preferred aqueous solution is saline solution containing salts including one or more other ingredients known to a person skilled in the art. Examples of other ingredients include without limitation, suitable buffer agents, tonicity agents, water-soluble viscosity builders, surfactants, antibacterial agents, preservatives, and lubricants (e.g., cellulose derivatives, polyvinyl alcohol, polyvinyl pyrrolidone).

The pH of a packaging solution should be maintained within the range of about 6.0 to 8.0, preferably about 6.5 to 7.8. Examples of physiologically compatible buffer systems include, without limitation, acetates, phosphates, borates, citrates, nitrates, sulfates, tartrates, lactates, carbonates, bicarbonates, tris, tris derivative, and mixtures thereof. The amount of each buffer agent is that amount necessary to be effective in achieving a pH of the composition of from 6.0 to 8.0.

Typically, the aqueous solutions for packaging and storing contact lenses are also adjusted with tonicity adjusting agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 400 mOsm/kg and more preferably between about 250 to about 350 mOsm/kg, and most preferably between about 280 to about 320 mOsm/kg.

Examples of the preservative may be benzalkonium chloride and other quaternary ammonium preservative agents, phenylmercuric salts, sorbic acid, chlorobutanol, disodium edetate, thimerosal, methyl and propyl paraben, benzyl alcohol, and phenyl ethanol.

Surfactants can be virtually any ocularly acceptable surfactant including non-ionic, anionic, and amphoteric surfactants. Examples of preferred surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of $C_{12}$-$C_{18}$ alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

The base of a container of the invention may be formed from a variety of plastic materials, but is preferably transparent to allow the user to inspect the lens without opening the storage package. The plastic material should be capable of being sterilized at 120° C. without substantial loss of its physical properties of dimensional stability, warpage, and shrinkage. The plastic material should have low water and vapor permeability to prevent the evaporation and loss of the lens care solution. The plastic material should not be permeable to bacteria and oxygen in order to avoid contamination and to keep the efficacy of the solution. Preferably, plastic materials should have a high strength and a high tolerance, in view of the cost and efficiency in manufacturing the container body and easiness in handling the material.

Examples of plastic materials include without limitation fluoro-resin, polyamide, polyacrylate, polyethylene, nylons, olefin co-polymers (e.g., copolymers of polypropylene and polyethylene), polyethylene terephthalate, poly vinyl chloride, non-crystalline polyolefin, polycarbonate, polysulfone, polybutylene terephthalate, polypropylene, polymethyl pentene, polyesters, rubbers, urethanes, and the like. These materials are adopted solely or alternatively in a composite body or a laminar structure. The plastic material used to make the base is preferably polypropylene.

The base of a container of the invention is preferably prepared by injection molding or thermoforming. Containers made from hydrophobic plastic material may be in any desired forms. For example, a container of the invention can have any form of a conventional blister package known in the prior art.

The cavity of the base of a container of the invention may be suitably designed and sized with no limitation to receive the lens and the sufficient quantity of sterile preserving solution to completely submerge the lens. The cavity may have a variety of shapes in plane view, including a circular shape, a polygonal shape, an ellipsoidal shape, a heart shape, and the like. The surface of the cavity may be desirably shaped depending upon a specific configuration, size and the like of an ophthalmic lens to be received in the cavity. For instance, the surface of the cavity may have a hemisphere (concave) shape.

In accordance with the present invention, at least the surface of the cavity of a container is modified by surface treatment to hydrophilic so that deformations of the soft contact lenses, caused by mismatch in surface hydrophilicity between the cavity surface and the hydrophilic coating during autoclaving and/or by adherence of the soft contact lens to the cavity surface, are substantially reduced. The surface treatment can be performed by a variety of methods, including without limitation plasma treatment, plasma coating, corona discharge, LbL coating, flame treatment and acid surface etching treatment. Preferably, the surface treatment is corona discharge, plasma treatment, or LbL coating.

Typically, the base comprises a flange portion extending about the cavity containing a soft contact lens in a sterile packaging solution, so as to ensure that at least the cavity is appropriately sealed by a flexible cover sheet.

The cover sheet may be a single film or alternatively a multi-layered film, and any film may be adopted as the cover sheet as long as the film is capable of being sealed to the container base by bonding, welding or other similar methods. The flexible cover sheet may be formed of a variety of water-impermeable materials and may have a variety of thicknesses. The sheet must be sufficiently flexible to enable the user to easily remove the sheet from the container. The cover sheet is preferably a laminate material preferably comprising a metal foil layer and at least one, preferably two polymer layers, e.g. polypropylene, coating the foil. The preferred foil is aluminum. Preferably, the sheet is formed from a metal (e.g., aluminum) foil or foil composite.

The cover sheet may be printed with information regarding the contact lens contained in the container or with other information for the end user or the dealer. The container may be affixed to the flexible cover sheet by a number of methods. However, the strength of the bond between the container and sheet should not be excessive, i.e., the user should be able to easily and quickly separate the sheet from the container. For example, the cover sheet can be sealed to the base or flange thereof by means of temperature or ultrasonic treatment or by another appropriate adhesion method.

It should be understood that a plurality of base parts, e.g., four base parts, advantageously form one unit, so that handling of the base parts in the manufacturing process is simplified.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for sterilizing a soft contact lens and providing a sterilized storage package of the soft contact lens maintained in a packaging solution, comprising the steps of:
   (a) providing a container having a cavity for receiving a packaging solution and a soft contact lens having a core polymeric material and a hydrophilic coating thereon, wherein the cavity has a cavity surface which is modified by surface treatment to hydrophilic so that deformations of the soft contact lenses, caused during autoclaving by air bubbles formed between the cavity surface and the hydrophilic coating due to mismatch in surface hydrophilicity and/or by adherence of the soft contact lens to the cavity surface, are substantially reduced;

(b) placing an amount of the packaging solution and the soft contact lens in the container, wherein the amount of the packaging solution is sufficient to have the soft contact lens to be fully immersed;

(c) sealing the container with a flexible cover sheet which is a laminate material comprising a metal foil layer and at least one polymer layer to form a storage package of the soft contact lens; and (d) autoclaving the package to obtain the sterilized storage package of the soft contact lens.

2. The method of claim 1, wherein the surface treatment is plasma treatment, plasma coating, corona discharge, LbL coating, flame treatment, or acid surface etching treatment.

3. The method of claim 2, wherein the surface treatment is corona discharge or LbL coating.

4. The method of claim 1, wherein the core polymeric material is a silicon hydrogel.

5. The method of claim 4, wherein the silicone hydrogel is prepared by curing in a mold a polymerizable composition comprising a siloxane-containing macromer and/or a siloxane-containing monomer.

6. The method of claim 4, wherein the silicon hydrogel is prepared by curing in a mold a formulation for making soft contact lenses selected from the group consisting of the formulations of lotrafilcon A, lotrafilcon B and balafilcon.

7. The method of claim 1, wherein the core polymeric material is a silicone elastomer, a fluorohydrogel, or a fluorosilicone hydrogel.

8. The method of claim 4, wherein the packaging solution is a water-based solution.

9. The method of claim 8, wherein the packaging solution is a buffered saline solution having a pH of from about 6.0 to 8.0 and includes buffer agents selected from the group consisting of acetates, phosphates, borates, citrates, nitrates, sulfates, tartrates, lactates, carbonates, bicarbonates, tris, tris derivative, and mixtures thereof.

10. The method of claim 8, wherein the packaging solution includes one or more ingredients selected from the group consisting of suitable buffer agents, tonicity agents, water-soluble viscosity builders, surfactants, antibacterial agents, preservatives, and lubricants, and combinations thereof.

11. The method of claim 4, wherein the packaging solution comprises cellulose derivatives, polyvinyl alcohol, polyvinyl pyrrolidone, or a combination thereof.

12. The method of claim 11, wherein the packaging solution comprises cellulose derivatives.

13. The method of claim 11, wherein the packaging solution comprises polyvinyl alcohol.

14. The method of claim 11, wherein the packaging solution comprises polyvinyl pyrrolidone.

15. The method of claim 8, wherein the packaging solution an osmotic value of from 200 to 400 mOsm/kg.

16. The method of claim 4, wherein the container comprises a base which includes the cavity and is made from a hydrophobic plastic material.

17. The method of claim 7, wherein the packaging solution comprises cellulose derivatives.

18. The method of claim 7, wherein the packaging solution comprises polyvinyl alcohol.

19. The method of claim 7, wherein the packaging solution comprises polyvinyl pyrrolidone.

20. The method of claim 19, wherein the hydrophobic plastic material comprises polypropylene.

21. The sterilized storage package, including the contact lens and the packaging solution, of claim 1.

22. A method of manufacturing a silicon hydrogel soft contact lens, comprising the steps of:

(a) forming the lens with a core polymeric material and a hydrophilic coating thereon;

(b) providing a container having a cavity with a cavity surface that is modified by surface treatment to hydrophilic;

(c) placing an amount of a packaging solution and the lens in the cavity of the container, wherein the amount of the packaging solution is sufficient to fully immerse the lens;

(d) sealing the container with a flexible cover sheet which is a laminate material comprising a metal foil layer and at least one polymer layer to form a storage package of the lens and the packaging solution; and (e) autoclaving the storage package to sterilize the lens packaging solution, wherein deformations of the lens caused during autoclaving by air bubbles being formed between the cavity surface and the lens due to mismatch in surface hydrophilicity, by adherence of the lens to the cavity surface, or both are substantially reduced by the matched hydrophilicity of the lens coating and the cavity surface.

* * * * *